United States Patent [19]
Hartman et al.

[11] Patent Number: 4,876,271
[45] Date of Patent: Oct. 24, 1989

[54] SUBSTITUTED THIENO[3,2-B]THIOPHENE-2-SULFONAMIDES AS TOPICALLY ACTIVE CARBONIC ANHYDRASE INHIBITORS

[75] Inventors: George D. Hartman, Lansdale; John D. Prugh, Chalfont, both of Pa.

[73] Assignee: Merck & Co., Inc., Rahway, N.J.

[21] Appl. No.: 286,822

[22] Filed: Dec. 20, 1988

[51] Int. Cl.$^4$ .................... C07D 495/04; A61K 31/38
[52] U.S. Cl. .................................... 514/443; 514/321; 514/253; 514/233.8; 514/228.2; 549/50; 546/197; 544/58.7; 544/61; 544/145; 544/377
[58] Field of Search .......................... 549/50; 546/197; 544/145, 61, 58.7, 377; 514/443, 321, 353, 228.2, 233.8

[56] References Cited

U.S. PATENT DOCUMENTS

| | | | |
|---|---|---|---|
| 3,733,322 | 5/1973 | Wright | 549/50 X |
| 4,677,115 | 6/1987 | Baldwin et al. | 514/432 |
| 4,720,503 | 1/1988 | Witzel et al. | 549/50 X |
| 4,798,831 | 1/1989 | Prugh et al. | 514/253 |
| 4,806,562 | 2/1989 | Hartman et al. | 514/443 |

Primary Examiner—Richard A. Schwartz
Assistant Examiner—E. B. Magrab
Attorney, Agent, or Firm—William H. Nicholson; Joseph F. DiPrima

[57] ABSTRACT

Novel substituted thieno[3,2-b]thiophene-2-sulfonamides are prepared by novel synthetic processes. These compounds are useful for the treatment of elevated intraocular pressure in compositions including ophthalmic drops and inserts.

10 Claims, No Drawings

SUBSTITUTED THIENO[3,2-B]THIOPHENE-2-SULFONAMIDES AS TOPICALLY ACTIVE CARBONIC ANHYDRASE INHIBITORS

SUMMARY OF THE INVENTION

This invention relates to thieno[3,2-b]thiophene-2-sulfonamides having novel substituents. These compounds are useful in the reduction of elevated intraocular pressure. More particularly this invention relates to compounds having the structural formula:

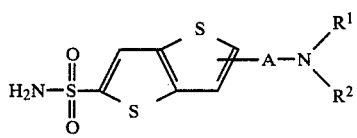

wherein A, R, $R_1$ and $R_2$ are hereinafter defined, as well as the pharmaceutically and ophthalmologically acceptable salts thereof. This invention also relates to pharmaceutical compositions for systemic and opthalmic use employing a novel compound of this invention as an active ingredient for the treatment of elevated intraocular pressure especially when accompanied by pathological damage such as in the disease known as glaucoma. This invention also relates to novel processes for the preparation of thieno[3,2-b]thio-phene-2-sulfonamides.

BACKGROUND OF THE INVENTION

Glaucoma is an ocular disorder associated with elevated intraocular pressures which are too high for normal function and may result in irreversible loss of visual function. If untreated, glaucoma may eventually lead to blindness. Ocular hypertension, i.e., the condition of elevated intraocular pressure without optic nerve head damage or characteristic glaucomatous visual field defects, is now believed by many ophthalmologists to represent the earliest phase of glaucoma.

Many of the drugs formerly used to treat glaucoma proved not entirely satisfactory. Indeed, few advances were made in the treatment of glaucoma since pilocarpine and physostigmine were introduced. Only recently have clinicians noted that many β-adrenergic blocking agents are effective in reducing intraocular pressure. While many of these agents are effective in reducing intraocular pressure, they also have other characteristics, e.g. membrane stabilizing activity, that are not acceptable for chronic ocular use. (S)-1-tert-Butylamino-3[(4-morpholino-1,2,5-thiadiazol-3yl)oxy]-2-propanol, a β-adrenergic blocking agent, was found to reduce intraocular pressure and to be devoid of many unwanted side effects associated with pilocarpine and, in addition, to possess advantages over many other β-adrenergic blocking agents, e.g. to be devoid of local anesthetic properties, to have a long duration of activity, and to display minimal tolerance.

Although pilocarpine, physostigmine and the β-blocking agents mentioned above reduce intraocular pressure, none of these drugs manifests its action by inhibiting the enzyme carbonic anhydrase and, thereby, impeding the contribution to aqueous humor formation made by the carbonic anhydrase pathway.

Agents referred to as carbonic anhydrase inhibitors, block or impede this inflow pathway by inhibiting the enzyme, carbonic anhydrase. While such carbonic anhydrase inhibitors are now used to treat intraocular pressure by oral, intravenous or other systemic routes, they thereby have the distinct disadvantage of inhibiting carbonic anhydrase throughout the entire body. Such a gross disruption of a basic enzyme system is justified only during an acute attack of alarmingly elevated intraocular pressure, or when no other agent is effective. Despite the desirability of directing the carbonic anhydrase inhibitor only to the desired ophthalmic target tissue, no topically effective carbonic anhydrase inhibitors are available for clinical use.

However topically effective carbonic anhydrase inhibitors are reported in U.S. Pat. Nos. 4,386,098; 4,416,890; 4,426,388; and 4,668,697, where the compounds reported therein are 5 (and 6)-hydroxy-2-benzothiazole-sulfonamides and acyl esters thereof and 5 (and 6)-hydroxy-2-sulfamoyl-benzothiophenes and esters thereof, and U.S. Pat. No. 4,677,115, where the compounds are reported to be 5,6-dihydro-thieno-thiophen-sulfonamides.

DETAILED DESCRIPTION OF THE INVENTION

The novel compounds of this invention have structural formula:

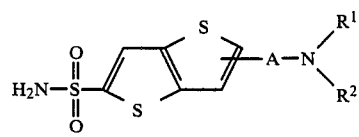

or an ophthalmologically or pharmaceutically acceptable salt thereof, wherein

A is $C_{1-8}$ alkylene, either straight or branched chain and either unsubstituted or substituted with $C_{1-3}$ alkoxy or hydroxy;

$R_1$ and $R_2$ are independently selected from:
(1) hydrogen;
(2) $C_{1-6}$ alkyl, either unsubstituted or substituted with one or more of the following:
  (a) $C_{1-3}$ alkoxy;
  (b) $C_{3-6}$ cycloalkyl;
  (c) hydroxy;
  (d) halo;
  (e) $C_{1-3}$ alkanol;
  (f) $C_{1-3}$ alkoxy-$C_{1-3}$ alkanol;
  (g) $C_{1-3}$ alkoxy-$(C_{2-4}$ alkoxy$)_n$ (wherein n=1–6);
  (h) —$S(O)_n$—$C_{1-3}$ alkyl (wherein n=0–2); or
  (i) —$NR^3R^4$, wherein $R^3$ and $R^4$ are independently selected from:
    (i) hydrogen;
    (ii) $C_{1-6}$ alkyl, either unsubstituted or substituted with one or more of $C_{1-3}$ alkoxy, hydroxy or phenyl;
    (iii) $C_{1-3}$ alkoxy—$C_{1-3}$ alkyl; or
    (iv) $C_{1-3}$ alkanol;
(3)

wherein $R^5$ is $C_{1-4}$ alkyl, either straight or branched chain and either unsubstituted or substituted with one or more of $C_{1-3}$ alkoxy, or hydroxy; or (4) taken together with the nitrogen atom to which they are attached form a 5-7 membered heterocycle, that may also contain an O, N or $S(O)_n$, wherein n=0-2, as one or more of the members, such as piperidino, morpholino, piperazino, N—$C_{1-3}$ alkylpiperazino, thiomorpholino, thiomorpholine-S-oxide or thiomorpholine-S,S-dioxide, A preferred embodiment of the novel compounds is that where A is joined to the 5-position of the thieno[3,2-b]thiophene ring system. It is still more preferred that A is —$(CH_2)$—$_{1-3}$, especially —$CH_2$—. It is also preferred that $R^1$ and $R^2$ are $C_{1-3}$ alkoxyethyl and/or $C_{1-3}$ alkoxy-$C_{2-4}$ alkoxyethyl.

Preferred species of the invention are:
5-Isobutylaminomethylthieno[3,2-b]thiophene-2-sulfonamide;
5-Methylaminomethylthieno[3,2-b]thiophene-2-sulfonamide;
5-(2-Methoxy)ethylaminomethylthieno[3,2-b]thiophene-2-sulfonamide;
5-[N,N-bis(2-Methoxyethyl)aminomethyl]thieno[3,2-b]thiophene-2-sulfonamide.

While any of a number of processes may be used to prepare these compounds, or to produce the various intermediates, the preferred processes for preparing the novel compounds of the invention are illustrated by the following schematic illustration:

SYNTHETIC SCHEME

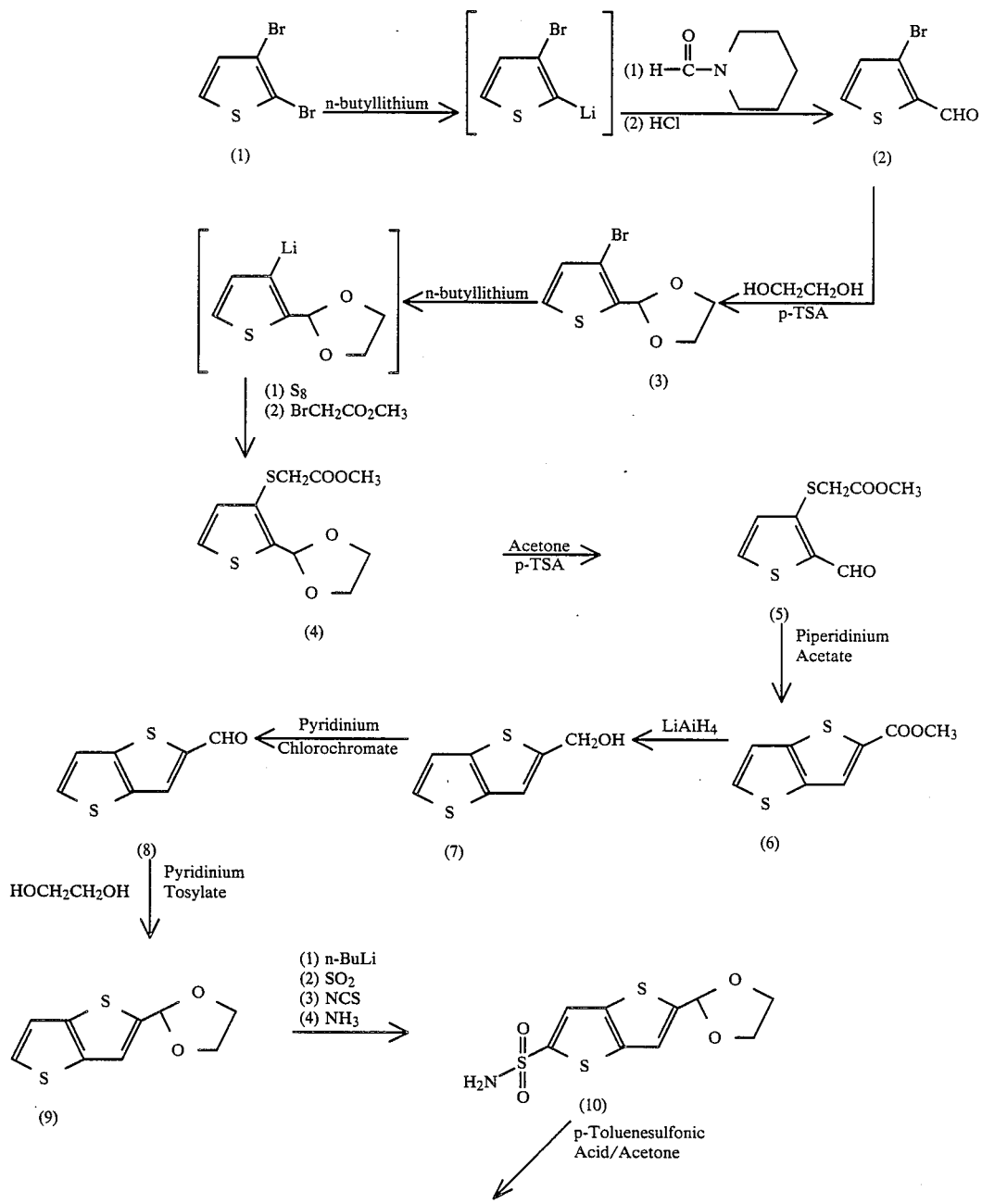

-continued
SYNTHETIC SCHEME

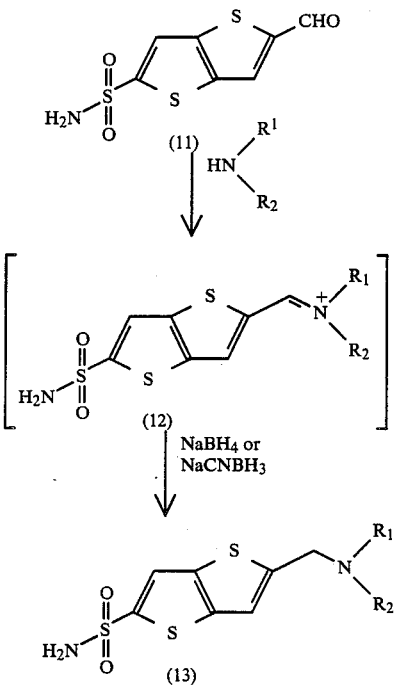

As illustrated above, novel substituted thieno[3,2-b]thiophene-2-sulfonamides of the present invention may be prepared by a novel series of reactions as follows:

2,3-Dibromothiophene (1) is converted to 3-Bromothiophene-2-carboxaldehyde (2) through a series of reactions with n-butyl lithium yielding 2-litho-3-bromothiophene, followed by N-formylpiperidine and 3N HCl. This 3-bromothiophene-2-carboxaldehyde (2) is then placed in toluene solution containing ethylene glycol to which is added pyridinium tosylate yielding 3-bromo-2-(2-dioxolanyl)thiophene (3). This 3-bromo-2-(2-dioxolanyl)thiophene (3) is then reacted with n-butyllithium followed by sulfur, then by methyl bromoacetate, to yield methyl 3-[2-(2-dioxolanyl)thiophene-3-yl]-3-thiapropionate (4). This methyl 3-[2-(2-dioxolanyl)thiophene-3-yl]-3-thiapropionate (4) is next dissolved in acetone and p-toluenesulfonic acid monohydrate is added in catalytic amount yielding methyl 3-(2-formylthiophene-3-yl)-3-thiapropionate (5). This methyl 3-(2-formylthiophene-3-yl)3-thiapropionate (5) is then treated in solution with piperidinium acetate yielding methyl thieno[3,2-b]thiophene-2-carboxylate (6). This methyl thieno[3,2-b]thiophene-2-carboxylate (6) is then placed in solution with lithium aluminum hydride yielding 2-hydroxymethylthieno[3,2-b]-thiophene (7). This 2-hydroxymethylthieno[3,2-b]-thiophene (7) is then added to a suspension of pyridinium chlorochromate in methylene chloride and yields thieno[3,2-b]thiophene-2-carboxaldehyde (8). This thieno[3,2-b]thiophene-2-carboxaldehyde (8) is then mixed with ethylene glycol, pyridinium tosylate and benzene yielding 2-(2-dioxolanyl)thieno[3,2-b]thiophene (9). This 2-(2-dioxolanyl)thieno[3,2-b]thiophene (9) is then reacted with n-butyllithium after which $SO_2$ is bubbled onto the surface and N-chlorosuccinimide and $NH_4OH$ are added separately at the appropriate time. This series of steps yields 5-(2-dioxolanyl)thieno[3,2-b]thiophene-2-sulfonamide (10). This 5-(2-dioxolanyl)thieno[3,2-b]thiophene-2-sulfonamide (10) may then be reacted with p-toluenesulfonic acid monohydrate in acetone to yield 5-formylthieno[3,2-b]thiophene-2-sulfonamide (11). The 5-formylthieno[3,2-b]thiophene-2-sulfonamide (11) is then reacted with an appropriate amine yielding the intermediate iminium salt (12) which may then be reduced with $NaBH_4$ or $NaCNBH_3$ to give the desired 5-substituted thieno[3,2-b]thiophene-2-sulfonamide.

The hydrochloride salts of the present invention may be prepared by placing a 4 or 5-substituted alkylaminoalkyl (or alkoxyalkylamino alkyl)thieno[3,2-b]thiophene-2-sulfonamide in solution with hot ethanol and adding ethanolic HCl. After cooling, and if needed, ether treatment, a crystalline hydrochloride salt may be collected.

For use in treatment of conditions relieved by the inhibition of carbonic anhydrase, the active compound can be administered either systemically, or, in the treatment of the eye, topically. The dose administered can be from as little as 0.1 to 25 mg or more per day, singly, or preferably on a 2 to 4 dose per day regimen although a single dose per day is satisfactory.

When administered for the treatment of elevated intraocular pressure or glaucoma, the active compound is most desirably administered topically to the eye, although systemic treatment is, as indicated, also possible.

When given systemically, the drug can be given by any route, although the oral route is preferred. In oral administration, the drug can be employed in any of the usual dosage forms such as tablets or capsules, either in a contemporaneous delivery or sustained release form. Any number of the usual excipients or tableting aids can likewise be included.

When given by the topical route, the active drug or an ophthalmologically acceptable salt thereof such as the hydrochloride salt is formulated into an opthalmic preparation. In such formulations, from 0.1% to 15% by weight can be employed. The objective is to administer a dose of from 0.1 to 1.0 mg per eye per day to the patient, with treatment continuing so long as the condition persists.

The medicament in the novel topical ocular formulations comprises one of the novel compounds of this invention either alone or in combination with a β-adrenergic blocking agent such as timolol maleate or a parasympathomimetic agent such as pilocarpine. In such combinations each of the active agents is present in an amount approximating that found in its single entity formulations.

The active drugs of this invention are most suitably administered in the form of ophthalmic pharmaceutical compositions adapted for topical administration to the eye such as a suspension, ointment, or as a solid insert. Formulations of these compounds may contain from 0.01 to 15% and especially 0.5% to 2% of medicament. Higher dosages as, for example, about 10%, or lower dosages can be employed provided the dose is effective in reducing or controlling elevated intraocular pressure. As a unit dosage from between 0.001 to 10.0 mg, preferably 0.005 to 2.0 mg, and especially 0.1 to 1.0 mg of the compound is generally applied to the human eye, generally on a daily basis in single or divided doses so long as the condition being treated exists.

These hereinbefore described dosage values are believed accurate for human patients and are based on the known and presently understood pharmacology of the compounds, and the action of other similar entities in the human eye. They reflect the best mode known. As with all medications, dosage requirements are variable and must be individualized on the basis of the disease and the response of the patient.

The pharmaceutical preparation which contains the active compound may be conveniently admixed with a non-toxic pharmaceutical organic carrier, or with a non-toxic pharmaceutical inorganic carrier. Typical of pharmaceutically acceptable carriers are, for example, water, mixtures of water and water-miscible solvents such as lower alkanols or arylalkanols, vegetable oils, polyalkylene glycols, petroleum based jelly, ethyl cellulose, ethyl oleate, carboxymethylcellulose, polyvinylpyrrolidone, isopropyl myristate and other conventionally employed acceptable carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetraacetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like.

The pharmaceutical preparation may also be in the form of a solid insert such as one which after dispensing the drug remains essentially intact, or a bio-erodible insert that is soluble in lacrimal fluids, or otherwise disintegrates.

The following examples provide, by way of illustration, adequate means for the preparation of the novel compounds of the present invention. Alternative processes and process steps should be apparent from this description to those of ordinary skill in the art.

EXAMPLE 1

Step A

3-Bromothiophene-2-Carboxaldehyde (2)

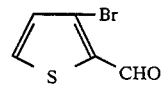

n-Butyllithium dissolved in hexane (2.3M; 44.3 mL; 0.102 mole) was added at a slow drip from a syringe to a solution of 2,3-dibromothiophene (1) (24.2 g; 0.1 mole) in anhydrous ether (100 mL) maintained at −70° to −64° C. internal temperature. The mixture was stirred for 15 minutes at this temperature, followed by the addition of N-formylpiperidine (11.7 mL; 11.95 g., 0.105 mole) at a slow drip over approximately 20 minutes maintaining a reaction temperature of −70° C. Stirring was continued at −70° C. for 30 minutes. The cold bath was removed and stirring was continued at ambient temperature until internal temperature rose to 0° C. 3N HCl (50 mL) was added while keeping the internal temperature at 0° C. The mixture was then poured into a separatory funnel, adding about 50 mL of 3N HCl in the transfer, and shaken vigorously. The combined ether extracts were extracted with water first, then with saturated sodium bicarbonate solution and dried (MgSO₄). The ether solution was filtered and evaporated in vacuo to leave 18.73 g of crude 3-bromothiophene-2-carboxaldehyde (2) which was used in the next step without purification.

Step B

3-Bromo-2-(2-dioxolanyl)thiophene (3)

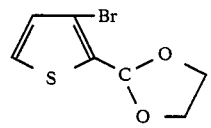

Pyridinium tosylate (1 g., 4 mmoles) was added to a mixture of 3-bromothiophene-2-carboxaldehyde (2) (18.7 g., 97.9 mmole), ethylene glycol (22 mL., 24.8 g., 400 mmole) and dry toluene (100 mL). The mixture was refluxed and the water removed by a Dean-Stark trap. After 1 hour, TLC (10% EtOAC/hexane) showed the reaction was complete. The mixture was cooled to room temperature and partitioned between ether (100 mL) and water (100 mL) components. The organic layer was separated and extracted with water (3×50 mL) and then with a saturated solution of sodium bicarbonate (25 mL). The resulting extract was dried (MgSO₄), filtered and evaporated in vacuo to leave 21.5 g. of crude product. This product was distilled to give 17.6 g of 3 -Bromo-2-(2-dioxolanyl)thiophene (3), bp: 86°-87° C./0.5 mm.

Calc. for C7H7BrO2S: C, 35.76; H, 3.00; Found: C, 36.01; H, 2.87.

Step C

Methyl 3-[2-(2-dioxolanyl)thiophene-3-yl]-3-thiapropionate (4)

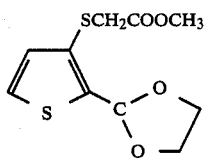

3-Bromo-2-(2-dioxolanyl)thiophene (3) (47.02 g, 0.2 moles) was dissolved in dry THF (600 mL) under N2 and cooled to −105° C., internal temperature (cooling bath composed of methanol and ether equal parts, frozen to a slush with liquid N2). n-Butyl lithium (83 mL or a 24 m solution hexane; (0.2 moles) was added at a rapid drip while maintaining the internal temperature at −96° C. to −105° C. for 5 minutes. Sulfur was then added (6.57 g., 205 mmoles) all at once. The cooling bath was removed and the mixture allowed to warm to −78° C. until all but excess sulfur was consumed. (Not longer than 15 min.). The mixture was cooled to −90° C. and methyl bromoacetate (19 mL, 31 L g., 204 mmoles) was added at a rapid drip. The mixture was allowed to warm to −78° C. and held there for 15 minutes. The cooling bath was removed and the mixture was stirred at ambient temperature until the internal temperature rose to 0° C. A warming bath was then used to warm internal temperature to room temperature. THF was evaporated in vacuo and the residue was dissolved in ether and extracted with water four times, dried (MgSO4), filtered and the solvent evaporated in vacuo to leave 53.73 g. of crude methyl-3-[2-(2-dioxolanyl)thiophene-3-yl]-3-thiapropionate (4).

Step D

Methyl 3-(2-formylthiophen-3-yl)-3-thiapropionate (5)

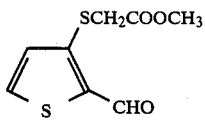

Methyl-3-[2-(2-dioxolanyl)thiophene-3-yl]-3-thiapropionate (4) (117.63 g, 0.515 mole) was dissolved in acetone (500 mL), and p-tolunesulfonic acid hydrate (1.30 g., 6.83 mmole) was added and stirred over 1 hour. A saturated solution of sodium bicarbonate (20 mL) was added followed by water (250 mL). The acetone was evaporated leaving a tacky solid in water. This tacky solid was dissolved in ether and washed with water four times, dried (MgSO4), filtered and the solvent evaporated in vacuo to leave 96.91 g of crude methyl 3-(2-formylthiophen-3-yl)-3-thiapropionate (5) which was used in the next step without purification.

Step E

Methyl thieno[3,2-b]thiophene-2-carboxylate (6)

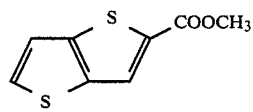

Piperidine (37.9 g., 445 mmoles) was added to a solution of acetic acid (26.7 g., 445 mmole) in benzene (1 L) and stirred for 5 minutes. Methyl 2-formylthiophen-3-yl-3-thiapropionate (5) (96.91 g., 448 mmoles) was added in benzene to a total volume of benzene (2.2 L). The solution was refluxed while stirring and water was collected via a Dean-Stark trap. After 5 hours of reflux, 7.8 ml of water was collected. The mixture was cooled to room temperature and extracted with water two times, then 1N.HCl followed by water, and then by a saturated solution of sodium bicarbonate two times. The resulting benzene solution was dried (MgSO4), filtered and evaporated to leave 88 g. of crude product. This was extracted with room temperature ether, then three times with boiling ether, leaving a tarry gum. Silica gel (100 g.) was added to the ether solution of the product. The solvent was evaporated and the clumps broken up leaving a free flowing product adsorbed on silica gel. This was chromatographed on silica gel eluting with 50% hexane in toluene. The solvent was evaporated from the fractions containing the product and after trituration with hexane, 36.93 g. of methyl thieno[3,2-b]thiophene-2-carboxylate (6), mp 96°–97° C. was isolated.

Calc. for C8H6O2S2: C, 48.47; H, 3.05; Found: C, 48.85; H, 3.14.

Step F

2-Hydroxymethylthieno[3,2-b]thiophene (7)

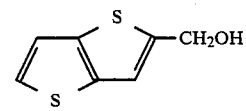

A solution of methylthieno[3,2-b]thiophene-2-carboxylate (6) (37.04 g., 186.9 mmoles) in ether (850 mL) was added at a rapid drip (1 hr. 45 min.) to a suspension of lithium aluminum hydride (14.18 g., 373.7 mmoles) in ether (500 mL) which had been cooled in an ice-water bath. After the addition was completed, the mixture was stirred at room temperature for three hours. The reaction was worked up by cooling in an ice-water bath with successive dropwise addition of water (14 mL), 15% aqueous sodium hydroxide (14 mL) and water (42 mL) with vigorous stirring. Vigorous stirring was continued until the salts are well granulated. The ether solution of the product was decanted and the salts washed further with ether. The combined ether solutions were dried (MgSO4), filtered, and the solvent evaporated in vacuo to leave 31.4 g of 2-hydroxymethylthieno[3,2-b]thiopene (7) (mp 91° to 93° C.) which was used in the next step without purification. A small sample was recrystallized from hexane for analysis (mp 93°–94° C.).

Calc. for C7H6OS2: C, 49.38; H, 3.55; Found: C, 49.24; H, 3.47.

Step G

Thieno[3,2-b]thiophene-2-carboxaldehyde (8)

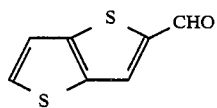

A solution of 2-hydroxymethylthieno[3,2-b]thiophene (7) (31.4 g., 184 mmole) in methylene chloride (430 mL) was added all at once to a stirred suspension of pyridinium chlorochromate (59.5 g., 276 mmole) which had been ground in a mortar and pestle and partially dissolved in methylene chloride with vigorous stirring. Stirring was continued for 2 hours, at which point TLC (30% ethyl acetate in hexane on silica gel) showed the reaction about 60% complete. Pyridinium chlorochromate (15.86 g., 73.6 mmole) was added and the mixture stirred vigourously for 30 minutes. The solution was worked up by adding ether (2 L) and then filtering through an 80×300 mm column of silica gel. The gum in the flask was washed with ether (3×300 ml) and these washings passed through the column. The combined ether and methylene chloride solvents were evaporated in vacuo to leave 24.79 g of crude dark purple product which was sublimed at bath temperature 100°–107° C. at 0.1 mm pressure to give 23.30 g. of white crystalline thieno[3,2-b]thiophene-2-carboxaldehyde (8), mp 53°–54° C.

Calc. for $C_7H_4OS_2$: C, 49.98; H, 2.40; Found: C, 49.95; H, 2.33.

Step H 2-(2-dioxolanyl)thieno[3.2-b]thiophene (9)

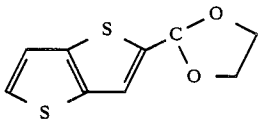

A mixture of thieno[3,2-b]thiophene-2-carboxaldehyde (8) (23.30 g., 138.5 mmole); ethylene glycol (31 mL., 34.39 g., 554.0 mmole); pyridinium tosylate (2.5 g., 10 mmole); and benzene (200 mL) was stirred and refluxed and the water (3.2 mL) was removed by a Dean-Stark trap (~4 hours). The reaction was cooled to room temperature, extracted with water three times and then with a saturated solution of sodium bicarbonate. The organic layer was dried (MgSO4), filtered, and the solvent was evaporated to leave a crystalline mass. Trituration with a small amount of ether removed the color to give 24.72 g of a white crystalline product, mp. 88°–90° C. An additional 1.43 g of product was collected from the ether washing, mp 88°–89° C., yielding a total of 26.15 g of 2-(2-dioxolanyl)thieno[3,2-b]thiophene (9). This product was used in the next step without further purification.

Step I 5-(2-dioxolanyl)thieno[3,2-b]thiophene-2-sulfonamide (10)

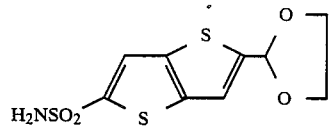

To 1.0 g (4.72 mmoles) 2-(2-dioxolanyl)thieno [3,2-b]thiophene (9) in 10 mL THF cooled to −78° C. under $N_2$ was added 4.72 mmoles n-butyllithium(hexane) dropwise at < −70° C. and the clear amber solution was stirred at −78° C. for 45 minutes during which time the reaction mixture become a tan suspension. Sulfur dioxide gas was then bubbled onto the surface of this suspension and the temperature was maintained at −65° C. for 0.5 hr. The temperature was then allowed to gradually rise to −10° C. over 0.5 hours and the $SO_2$ was stopped. The solvent was then removed at <30° C. under vacuum to provide a brown solid that was dissolved in 10 mL saturated $NaHCO_3$. This was cooled to 0°–10° C. and 0.86 g (6.5 mmoles) N-chlorosuccinimide was added portionwise and stirring was continued for 1.5 hr. The reaction mixture was then extracted with 2×40 mL portions of ethyl acetate. The combined organics were washed with water, brine and then were dried and stripped to give the sulfonyl chloride as a tan solid. This was dissolved in 20 mL acetone, cooled to 0°–10° C. and treated with 5 mL concentrated $NH_4OH$ added in one portion. This was stirred for 45 minutes and after removing most of the actone in vacuo, 10 mL $H_2O$ was added to give a tan solid. This solid was collected, washed well with cold water and dried to provide 5-(2-dioxolanyl)thieno[3,2-b]thiophene-2-sulfonamide (10).

$^1$NMR(DMSO) δ 4.00(4H, dd), 6.13(1H, S), 7.62(1H, S), 7.79(2H, bs), 7.92(1H, S).

Step J

5-Formylthieno[3,2-b]thiophene-2-sulfonamide (11)

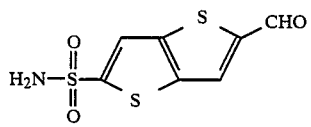

5-(2-Dioxolanyl)thieno[3,2-b]thiophene-2-sulfonamide (10) 8.50 g (0.029 moles) was dissolved in 500 mL acetone at room temperature and 0.9 g p-toluenesulfonic acid monohydrate was added in one portion. After 5 hours at room temperature all starting material was consumed. The reaction was quenched with 125 ml saturated $NaHCO_3$ solution and the acetone was stripped on a rotary evaporator. The resulting viscous mass was extracted with 3×300 mL ethyl acetate and these combined extracts were dried and stripped to give 6.55 g (91%) of 5-Formylthieno[3,2-b]thiophene-2-sulfonamide (11) as a tan solid, mp. 203°–204° C.

Step K

5-Isobutylaminomethylthieno[3,2-b]thiophene-2-sulfonamide (13)

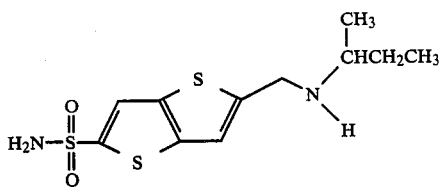

Isobutylamine (1.4 mL., 1.0 g., 14 mmoles) was added to a stirred suspension of 5-formylthieno[3,2-b]thiophene-2-sulfonamide (11) in methanol (5 mL). Stirring was contined and when a solution was obtained, 0.7 mL of a 5.75 m solution of HCl in methanol was added. When the imine began to crystallize, the flask was tightly stopped and shaken and heated with a heat gun to near reflux. The mixture was then stirred and allowed to cool slowly. After 30 minutes, formation of the imine was completed. The mixture was cooled in an ice-water bath and sodium borohydride (0.30 g., 8 mmoles) was added in one portion and the mixture stirred at room temperature for 1.5 hours. The reaction was worked up by evaporating the solvent in vacuo, adding water (10 mL) and enough concentrated HCl (2 ml) to make the mixture strongly acidic (or 2 mL). The mixture was swirled from time to time during a 10 minute interval. Concentrated $NH_4OH$ was added until the pH reached approximately 9 (or 2 mL). The solution was swirled for about 10 minutes to convert salt to free base. Crystals were collected and washed with water and dried to give 0.57 of 5-Isobutylaminomethylthieno[3,2-b]thienophene-2-sulfonamide (13) which was used in the next step directly.

Step L

5-Isobutylaminomethylthieno[3,2-b]thiophene-2-sulfonamide hydrochloride

5-Isobutylaminomethylthieno[3,2-b]thiophene-2-sulfonamide (0.57 g., 1.087 mmoles) was dissolved in boiling ethanol (30 mL), filtered, and cooled. Ethanolic HCl (5.10M) (0.6 mL., 3.05 mmoles) was added and the reaction stirred to make fine crystals. After cooling in the freezer for one hour, crystals were collected and washed with ethanol, and then with ether to give 0.54 g., of 5-Isobutylaminomethylthieno[3,2-b]thiophene-2-sulfonamide hydrochloride, (mp 257°–259° C.) (D).

Calc. for $C_{11}H_{17}ClN_2O_2S_3$: C, 38.75; H, 5.03; N, 8.22; Found: C, 38.58; H, 4.89; N, 8.22.

EXAMPLE 2

Step A

5-Methylaminomethylthieno[3,2-b]thiophene-2-sulfonamide

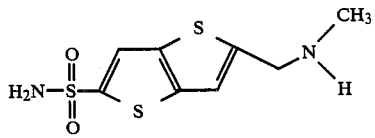

The procedure of Example I was followed except that in Step K methanolic methylamine (3.60M., 3.9 mL., 14 mmoles) was substituted for isobutylamine and methanol (2.5 mL) for methanol (5 mL) to give 0.53 g of 5-Methylaminomethylthieno[3,2-b]thiophene-2-sulfonamide.

Step B

5-Methylaminomethylthieno[3,2-b]thiophene-2-sulfonamide hydrochloride

5-Methylaminomethylthieno[3,2-b]thiophene-2-sulfonamide (0.53 g., 2.0 mmoles) was dissolved in boiling ethanol (75 mL), filtered and the ethanolic solution concentrated to 50 mL. Ethanolic HCl (5.10M., 0.43 mL., 2.2 mmoles) was added to the warm solution and the flask swirled to make fine crystals. The flask was cooled in the freezer for 1.5 hours. Crystals were collected and washed with cold ethanol, and then with ether, to give 0.50 g of 5-methylaminomethylthieno[3,2-b]thiophene-2-sulfonamide hydrochloride, mp 245°–250° C. (D).

Calc. for $C_8H_{11}ClN_2O_2S_3$: C, 32.15; H, 3.37; N, 9.37; Found: C, 32.08; H, 3.69; N, 9.44.

EXAMPLE 3

Step A

5-[(2-Methoxyethyl)aminomethyl]thieno[3,2-b]thiophene-2-sulfonamide

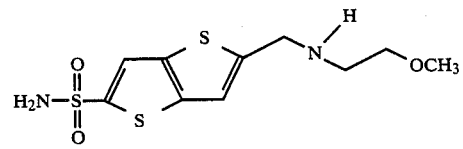

The procedure of Example I was followed except that in Step K 2-methoxethylamine was substituted for isobutylamine to give 0.50 g. of 5-[(2-Methoxy)ethylaminomethyl]thieno[3,2-b]thiophene-2-sulfonamide.

Step B

5-[(2-Methoxyethyl)aminomethyl]thieno[3,2-b]thiophene-2-sulfonamide hydrochloride The procedure of Example I was followed except that in Step L 5-[(2-methoxy)ethylaminomethyl]thieno[3,2-b]thiophene-2-sulfonamide was substituted for 5-isobutylaminomethylthieno[3,2-b]thiophene-2-sulfonamide to give 0.46 g of 5-[(2-methoxy)ethylaminomethyl]thieno[3,2-b]thiophene-2-sulfonamide hydrochloride, mp 224°–225° C. (D).

Calc. for $C_{10}H_{15}ClN_2O_3S_3$: C, 35.03; H, 4.41; N, 8.17; Found: C, 35.05; H, 4.71; N, 8.17.

EXAMPLE 4

Step A

5-[N,N-bis(2-Methoxyethyl)aminomethyl]thieno[3,2-b]thiophene-2-sulfonamide

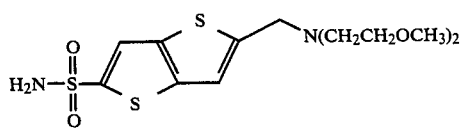

Methanolic HCl (2.7 mL of a 5.10M sol., 14 mmoles) was added to a solution of N,N-bis(2-methoxyethyl)a- mine. The solution was stirred for 15 minutes followed by the addition of 5-formylthieno[3,2-b]thiophene-2-sulfonamide (11) (0.742 g,. 3 mmole). The mixture was stirred at room temperature for 24 hours. Sodium cyanoborohydride (0.19 g., 3 mmoles) was added and the mixture was stirred for 24 hours. The mixture was cooled in ice water bath and sodium borohydride (0.38 g., 10 mmoles) was added in divided portions followed by stirring for 2 hours. The reaction was worked up by adding water (20 mL) and evaporating the methanol in vacuo to leave 1 g of crude product. The mixture was chromatographed on a 40×150 mm silica gel column eluting with 7% methanol in chloroform to give 0.66 g of 5-[N,N-bis(2-methoxyethyl)aminomethyl]thieno[3,2-b]thiophene-2-sulfonamide.

Step B

5-[N,N-bis(2-Methoxyethyl)aminomethyl]thieno[3,2-b]thiophene-2-sulfonamide hydrochloride A solution of 5-[N,N-bis(2-methoxyethyl)aminomethyl]thieno[3,2-b]thiophene-2-sulfonamide (0.66 g., 1.81 mmole) in ethanol (75 mL) was filtered and to this was added ethanolic HCl (0.71 mL of a 5.10M solution, 3.62 moles) swirled and let stand for 2 minutes. The solution was boiled down to a volume of 25 mL and cooled to a warm solution. Filtered ether was added with swirling until the hydrochloride came out of solution from a total volumn of about 75 mL. Crystals were collected and washed with ether to give 0.48 g. of 5-[N,N-bis(2-Methoxyethyl)aminomethyl]thieno[3,2-b]thiophene-2-sulfonamide hydrochloride mp 138°–140° C. (D).

Calc. for $C_{13}H_2ClN_2O_4S_3$: C, 38.94; H, 5.28; N, 6.99; Found: C, 38.97; H, 4.93; N, 6.97.

EXAMPLE 5

| 5-isobutylaminomethylthieno-[3,2-b]thiophene-2-sulfonamide hydrochloride | 1 mg | 15 mg |
|---|---|---|
| Monobasic sodium phosphate $H_2O$ | 9.38 mg | 6.10 mg |
| Dibasic sodium phosphate $.12H_2O$ | 28.48 mg | 16.80 mg |
| Benzalkonium chloride | 0.10 mg | 0.10 mg |
| Water for injection q.s. ad | 1.0 ml | 1.0 ml |

The novel compound, phosphate buffer salts, and benzalkonium chloride are added to and dissolved in water. The pH of the composition is adjusted to 5.4–7.4 and diluted to volume. The composition is rendered sterile by ionizing radiation.

EXAMPLE 6

| 5-Methylaminomethylthieno-[3,2-b]thiophene-2-sulfonamide hydrochloride | 1 mg |
|---|---|
| Hydroxypropylcellulose q.s. | 12 mg |

Ophthalmic inserts are manufactured from compression molded films which are prepared on a Carver Press by subjecting the powdered mixture of the above ingredients to a compressional force of 12,000 lbs. (gauge) at 300° F. for one to four minutes. The film is cooled under pressure by having cold water circulate in the platen. Ophthalmic inserts are then individually cut from the film with a rod-shaped punch. Each insert is placed into a vial, which is then placed in a humidity cabinet (88% R.H. at 30° C) for two to four days. After removal from the humidity cabinet, the vials are stoppered and then capped. The vials containing the hydrate insert are then autoclaved at 250° F. for ½ hour.

In the manner thus described and having knowledge common to one of ordinary skill in the art, compounds having the following substituents are prepared.

| Substituent Position | $R^1$ | $R^2$ |
|---|---|---|
| 5 | i-propyl | n-butyl |
| 5 | —H | —CH$_2$—(cyclobutyl) |
| 4 | —CH$_3$ | —CH$_2$—(cyclopentyl) |
| 5 | —CH$_2$CH$_2$OCH$_2$CH$_3$ | —CH$_2$—(cyclohexyl) |
| 4 | —CH$_2$CH$_2$OCH$_2$CH$_3$ | —CH$_2$—(cyclohexyl) |
| 5 | —CH$_2$CHOHCH$_2$OH | —CH$_2$CH$_2$OCH$_3$ |
| 4 | —CH$_2$CHOHCH$_2$OH | —CH$_2$CH$_2$OCH$_3$ |
| 5 | —CH$_2$CH$_2$CH$_2$OCH$_2$CH$_2$CH$_3$ | —CH$_2$CH$_2$F |
| 4 | —(CH$_2$)$_3$O(CH$_2$)$_2$CH$_3$ | —CH$_2$CH$_2$CH$_2$F |
| 5 | —CH$_2$CHOHCH$_3$ | —CH$_2$CH$_2$F |
| 4 | —CH$_2$CHOHCH$_3$ | —CH$_2$CH$_2$F |
| 5 | —CH$_2$CH$_2$S(=O)CH$_3$ | —CH$_2$CH$_2$OCH$_3$ |
| 4 | —CH$_2$CH$_2$S(=O)CH$_3$ | —CH$_2$CH$_2$OCH$_3$ |
| 5 | —CH$_2$CHOHCH$_2$CH$_2$S(=O)CH$_3$ | —CH$_2$CH$_2$F |
| 4 | —CH$_2$CHOHCH$_2$CH$_2$S(=O)CH$_3$ | —CH$_2$CH$_2$F |
| 5 | —CH$_2$CHOCH$_3$CH$_2$OH | —CH$_2$CH$_2$S(=O)$_2$CH$_3$ |
| 5 | —CH$_2$CH$_2$N(CH$_2$CH$_2$OCH$_3$)CH$_3$ | —CH$_2$CH$_2$F |
| 4 | —CH$_2$CH$_2$N(CH$_2$CH$_2$OCH$_3$)CH$_3$ | —CH$_2$CH$_2$F |
| 5 | —CH$_2$CH$_2$N(CH$_2$CH$_2$OH)(CH$_2$CH(OCH$_3$)CH$_2$OCH$_3$) | —CH$_2$—(cyclopropyl) |
| 4 | —CH$_2$CH$_2$N(CH$_2$CH$_2$OH)(CH$_2$CH(OCH$_3$)CH$_2$OCH$_3$) | —CH$_2$—(cyclopropyl) |

-continued

| Substituent Position | R¹ | R² |
|---|---|---|
| 5 | —CH₂CH₂N(morpholino-O) | H |
| 4 | —CH₂CH₂N(morpholino-O) | H |
| 5 | —CH₂CH₂N(ring-S(O)ₙ) | —CH₂CH₂OCH₃ |
| 4 | —CH₂CH₂N(ring-S(O)ₙ) | —CH₂CH₂OCH₃ |

What is claimed is:

1. A compound of the structural formula:

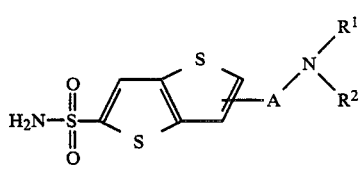

or ophthalmologically or pharmaceutically acceptable salt thereof, wherein

A is $C_{1-8}$ alkylene, either straight or branched chain and either unsubstituted or substituted with $C_{1-3}$ alkoxy or hydroxy;

$R_1$ and $R_2$ are independently selected from:
(1) hydrogen;
(2) $C_{1-6}$ alkyl, either unsubstituted or substituted with one or more of the following:
  (a) $C_{1-3}$ alkoxy;
  (b) $C_{3-6}$ cycloalkyl;
  (c) hydroxy;
  (d) halo;
  (e) $C_{1-3}$ alkanol;
  (f) $C_{1-3}$ alkoxy-$C_{1-3}$ alkanol;
  (g) $C_{1-3}$ alkoxy-$(C_{2-4}$ alkoxy$)_n$ (wherein n=1–6)
  (h) —S(O)ₙ—$C_{1-3}$ alkyl (wherein n=0–2); or
  (i) —NR₃R₄, wherein $R^3$ and $R^4$ are independently selected from:
    (i) hydrogen;
    (ii) $C_{1-3}$ alkyl, either unsubstituted or substituted with one or more of $C_{1-3}$ alkoxy or hydroxy;
    (iii) $C_{1-3}$ alkoxy-$C_{1-3}$ alkyl; or
    (iv) $C_{1-3}$ alkanol;
(3)

wherein $R^5$ is $C_{1-4}$ alkyl, either straight or branched chain and either unsubstituted or substituted with one or more of $C_{1-3}$ alkoxy, or hydroxy; or
(4) taken together with the nitrogen atom to which they are attached form a heterocycle selected from the group, piperidino, morpholino, piperazino, N-$C_{1-2}$ alkyl piperazino, thiomorpholino, thiomorpholine-S-oxide and thiomorpholine-S,S-dioxide.

2. The compound of claim 1 wherein $R_1$ is hydrogen and $R_2$ is $C_{1-4}$ alkyl.

3. The compound of claim 1 wherein $R_1$ is hydrogen and $R_2$ is $C_{1-3}$ alkoxy-$C_{2-4}$ alkyl.

4. The compound of claim 1 wherein $R_1$ and $R_2$ are independently chosen from C-3 alkoxyalkyl and $C_{1-3}$alkoxy-$C_{2-4}$ alkoxyethyl.

5. The compound of claim 1 wherein $R_1$ and $R_2$ are joined as described in claim 1 to form a heterocycle selected from the group, piperidino, morpholino, piperazino, N-$C_{1-3}$ alkyl piperazino, thiomorpholino, thiomorpholin-S-oxide and thiomorpholine-S,S-dioxide.

6. The compound of claim 1, which is:
5-Isobutylaminomethylthieno[3,2-b]thiophene-2-sulfonamide;
5-Methylaminomethylthieno[3,2-b]thiophene-2-sulfonamide;
5-(2-Methoxy)ethylaminomethylthieno[3,2-b]thiophene-2-sulfonamide;
5-[N,N-bis(2-Methoxyethyl)aminomethyl]thieno[3,2-b]thiophene-2-sulfonamide;
or pharmaceutically acceptable salts thereof.

7. An opthalmic composition for topical treatment of glaucoma and elevated intraocular pressure, comprising an ophthalmologically acceptable carrier and an effective intraocular pressure lowering amount of a compound with structural formula:

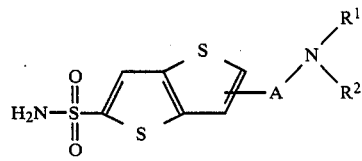

or an ophthalmologically acceptable salt thereof, wherein A, R, $R_1$ and $R_2$ are as defined in claim 1.

8. The composition of claim 7, wherein, wherein the compound is:
5-Isobutylaminomethylthieno[3,2-b]thiophene-2-sulfonamide;
5-Methylaminomethylthieno[3,2-b]thiophene-2-sulfonamide;
5-(2-Methoxy)ethylaminomethylthieno[3,2-b]thiophene-2-sulfonamide;
5-[N,N-bis(2-Methoxyethyl)aminomethyl]thieno[3,2-b]thiophene-2-sulfonamide;
or pharmaceutically acceptable salts thereof.

9. A method of treating glaucoma and elevated intraocular pressure which comprises topical ocular application to a patient in need of such treatment of an effective intraocular pressure lowering amount of a compound with structural formula:

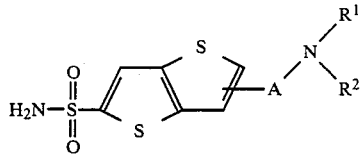

or an ophthalmolgically acceptable salt thereof, wherein A, R, $R_1$ and $R_2$ are as defined in claim 1.

10. The method of claim 9 wherein the compound is:
5-Isobutylaminomethylthieno[3,2-b]thiophene-2-sulfonamide;
5-Methylaminomethylthieno[3,2-b]thiophene-2-sulfonamide;
5-(2-Methoxy)ethylaminomethyl-thieno[3,2-b]thiophene-2-sulfonamide;
5-[N,N-bis(2-Methoxyethyl)aminomethyl]thieno[3,2-b]thiophene-2-sulfonamide;
or pharmaceutically acceptable salts thereof.

* * * * *